United States Patent
Lee et al.

(10) Patent No.: US 9,490,133 B2
(45) Date of Patent: Nov. 8, 2016

(54) ETCHING APPARATUS

(71) Applicant: Taiwan Semiconductor Manufacturing Company, Ltd., Hsin-Chu (TW)

(72) Inventors: Wan-Yu Lee, Taipei (TW); Ying-Hao Kuo, Hsin-Chu (TW); Hai-Ching Chen, Hsin-Chu (TW); Tien-I Bao, Dayuan Township (JP)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 416 days.

(21) Appl. No.: 13/749,119

(22) Filed: Jan. 24, 2013

(65) Prior Publication Data

US 2014/0206110 A1    Jul. 24, 2014

(51) Int. Cl.
| | |
|---|---|
| *H01L 21/00* | (2006.01) |
| *H01L 21/66* | (2006.01) |
| *G01R 31/26* | (2014.01) |
| *H01L 21/302* | (2006.01) |
| *H01L 21/461* | (2006.01) |
| *H01L 21/306* | (2006.01) |
| *H01L 21/67* | (2006.01) |
| *H01L 21/02* | (2006.01) |
| *H01L 21/311* | (2006.01) |

(52) U.S. Cl.
CPC ......... *H01L 21/306* (2013.01); *H01L 21/0206* (2013.01); *H01L 21/30608* (2013.01); *H01L 21/31133* (2013.01); *H01L 21/67086* (2013.01); *H01L 21/67253* (2013.01); *H01L 2924/0002* (2013.01)

(58) Field of Classification Search
None
See application file for complete search history.

(56) References Cited

U.S. PATENT DOCUMENTS

| | | | |
|---|---|---|---|
| 4,042,444 A * | 8/1977 | Snyder | 156/345.15 |
| 5,391,917 A | 2/1995 | Gilmour et al. | |
| 5,510,298 A | 4/1996 | Redwine | |
| 5,767,001 A | 6/1998 | Bertagnolli et al. | |
| 5,863,232 A | 1/1999 | Lee | |
| 5,964,629 A | 10/1999 | Park et al. | |
| 5,998,292 A | 12/1999 | Black et al. | |
| 6,027,255 A | 2/2000 | Joo et al. | |
| 6,048,256 A * | 4/2000 | Obeng | B24B 57/02 451/5 |
| 6,184,060 B1 | 2/2001 | Siniaguine | |

(Continued)

FOREIGN PATENT DOCUMENTS

| | | |
|---|---|---|
| CN | 1910486 | 2/2007 |
| TW | 201131229 | 9/2011 |
| TW | 201142391 | 12/2011 |

OTHER PUBLICATIONS

Xia et al., "The Influence of Oxidizing Agents on Etching and Passivation of Silicon in KOH Solution," Electrochimica Acta, 2000, vol. 45, pp. 4645-4653.

(Continued)

*Primary Examiner* — Calvin Choi
(74) *Attorney, Agent, or Firm* — Slater Matsil, LLP

(57) ABSTRACT

A system and method of etching a semiconductor device are provided. Etching solution is sampled and analyzed by a monitoring unit to determine a concentration of components within the etching solution, such as an oxidant concentration. Then, based upon such measurement, a makeup amount of the components may be added be a makeup unit to the etching solution to control the concentration of the components within the etching system.

20 Claims, 6 Drawing Sheets

(56) References Cited

U.S. PATENT DOCUMENTS

| | | |
|---|---|---|
| 6,322,903 B1 | 11/2001 | Siniaguine et al. |
| 6,448,168 B1 | 9/2002 | Rao et al. |
| 6,465,892 B1 | 10/2002 | Suga |
| 6,472,293 B1 | 10/2002 | Suga |
| 6,538,333 B2 | 3/2003 | Kong |
| 6,599,778 B2 | 7/2003 | Pogge et al. |
| 6,639,303 B2 | 10/2003 | Siniaguine |
| 6,664,129 B2 | 12/2003 | Siniaguine |
| 6,693,361 B1 | 2/2004 | Siniaguine et al. |
| 6,740,582 B2 | 5/2004 | Siniaguine |
| 6,800,930 B2 | 10/2004 | Jackson et al. |
| 6,807,204 B1 | 10/2004 | O'Dowd |
| 6,841,883 B1 | 1/2005 | Farnworth et al. |
| 6,882,030 B2 | 4/2005 | Siniaguine |
| 6,924,551 B2 | 8/2005 | Rumer et al. |
| 6,962,867 B2 | 11/2005 | Jackson et al. |
| 6,962,872 B2 | 11/2005 | Chudzik et al. |
| 7,030,481 B2 | 4/2006 | Chudzik et al. |
| 7,049,170 B2 | 5/2006 | Savastiouk et al. |
| 7,060,601 B2 | 6/2006 | Savastiouk et al. |
| 7,071,546 B2 | 7/2006 | Fey et al. |
| 7,111,149 B2 | 9/2006 | Eilert |
| 7,122,912 B2 | 10/2006 | Matsui |
| 7,157,787 B2 | 1/2007 | Kim et al. |
| 7,193,308 B2 | 3/2007 | Matsui |
| 7,262,495 B2 | 8/2007 | Chen et al. |
| 7,297,574 B2 | 11/2007 | Thomas et al. |
| 7,335,972 B2 | 2/2008 | Chanchani |
| 7,355,273 B2 | 4/2008 | Jackson et al. |
| 8,987,181 B2 | 3/2015 | Pollard et al. |
| 2004/0192050 A1 | 9/2004 | Yamashita |
| 2004/0238120 A1* | 12/2004 | Lin et al. ................ 156/345.11 |
| 2006/0239605 A1 | 10/2006 | Palen et al. |
| 2007/0058901 A1 | 3/2007 | Oohara et al. |
| 2007/0280585 A1 | 12/2007 | Warashina et al. |
| 2009/0022500 A1 | 1/2009 | Pinguet et al. |
| 2010/0025374 A1 | 2/2010 | Voipio |
| 2010/0092888 A1 | 4/2010 | Buchine et al. |
| 2010/0119231 A1 | 5/2010 | Kim et al. |
| 2010/0270650 A1 | 10/2010 | Li et al. |
| 2010/0273321 A1* | 10/2010 | Wang et al. ................ 438/514 |
| 2010/0320457 A1 | 12/2010 | Matsubara et al. |
| 2011/0303242 A1* | 12/2011 | Kimura et al. ................ 134/10 |
| 2012/0213470 A1 | 8/2012 | Matsuoka et al. |
| 2012/0263414 A1 | 10/2012 | Tan et al. |
| 2012/0329200 A1 | 12/2012 | Krishnan et al. |
| 2013/0223789 A1 | 8/2013 | Lee et al. |
| 2013/0295712 A1 | 11/2013 | Chen et al. |
| 2014/0057383 A1 | 2/2014 | Okuuchi |
| 2014/0206191 A1 | 7/2014 | Lee et al. |

OTHER PUBLICATIONS

Ma et al., "Polymer-Based Optical Waveguides: Materials, Processing, and Devices," Advanced Materials, Oct. 2, 2002, vol. 14, No. 19, pp. 1339-1365.

* cited by examiner

ETCHING APPARATUS

BACKGROUND

Generally, the etching of a substrate material, such as a silicon material, has been extensively utilized in the formation of various structures on the substrate and in the overall manufacturing of semiconductor devices. Such etching generally utilizes a photolithographic masking and etching process. In such a process a photoresist or hard mask is formed on the surface of the substrate and patterned in order to expose a portion of the substrate. Once the photoresist or hard mask has been placed and patterned, the underlying substrate that has been exposed by the hard mask or photoresist is exposed to an etchant by physically applying an etchant or etching solution to the exposed substrate.

Once in contact with the exposed portions of the substrate, the etchant or etching solution will begin to chemically react with the portions of the exposed substrate in which the etchant or etching solution is in contact. This chemical reaction chemically alters the exposed surface of the substrate and removes portions of the substrate from the surface of the substrate, thereby etching into the substrate as the chemical reaction proceeds. Because of the hard mask or photoresist, and the selectivity of the etchant or etching solution to the material of the substrate over the material of the hard mask or photoresist, the removal of material is controlled to occur only in those areas of the substrate that are uncovered and exposed by the hard mask or photoresist.

However, each etchant that may be utilized to remove material and form an opening into a material of a substrate, and each etching solution that may be utilized, have various benefits and problems. These include achieving a desired selectivity, obtaining a suitable process controllability, or even limiting the potential drawbacks of the etchant or etching solution.

BRIEF DESCRIPTION OF THE DRAWINGS

For a more complete understanding of the present embodiments, and the advantages thereof, reference is now made to the following descriptions taken in conjunction with the accompanying drawings, in which.

Corresponding numerals and symbols in the different figures generally refer to corresponding parts unless otherwise indicated. The figures are drawn to clearly illustrate the relevant aspects of the embodiments and are not necessarily drawn to scale.

DETAILED DESCRIPTION OF ILLUSTRATIVE EMBODIMENTS

The making and using of the present embodiments are discussed in detail below. It should be appreciated, however, that the present disclosure provides many applicable inventive concepts that can be embodied in a wide variety of specific contexts. The specific embodiments discussed are merely illustrative of specific ways to make and use the disclosed subject matter, and do not limit the scope of the different embodiments.

Embodiments will be described with respect to a specific context, namely a wet etching system to etch semiconductor material. Other embodiments may also be applied, however, to other etching systems and etching processes.

Figure 1:
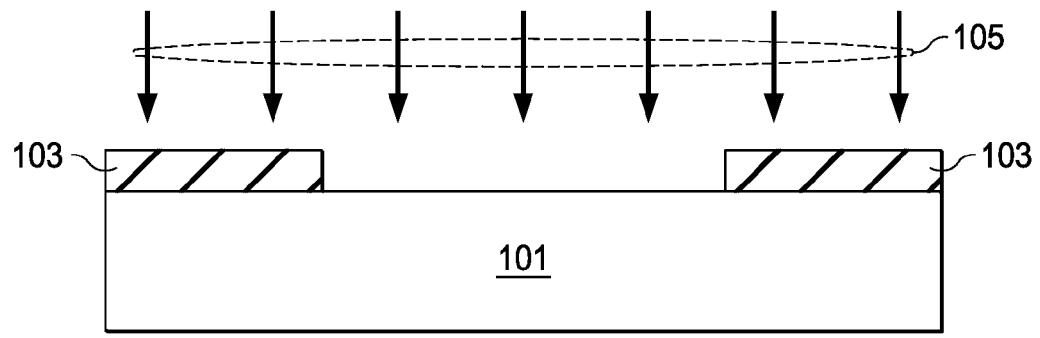
FIG. 1 illustrates a substrate and a patterned hard mask in accordance with an embodiment.

With reference now to FIG. 1, there is shown a cross-sectional, simplified view of a substrate 101 into which an opening 601 (not illustrated in FIG. 1 but illustrated and discussed below with respect to FIG. 6) will be formed. The substrate 101 may comprise a semiconductor material such as silicon, germanium, diamond, or the like, with a crystal orientation of (110) or (100). Alternatively, compound materials such as silicon germanium, silicon carbide, gallium arsenic, indium arsenide, indium phosphide, silicon germanium carbide, gallium arsenic phosphide, gallium indium phosphide, combinations of these, and the like, with other crystal orientations, may also be used. Additionally, the substrate 101 may comprise a silicon-on-insulator (SOI) substrate. Generally, an SOI substrate comprises a layer of a semiconductor material such as epitaxial silicon, germanium, silicon germanium, SOI, silicon germanium on insulator (SGOI), or combinations thereof. The substrate 101 may be doped with a p-type dopant, such as boron, aluminum, gallium, or the like, although the substrate may alternatively be doped with an n-type dopant, as is known in the art.

To form the opening 601 into the substrate 101, a hard mask 103 may be formed over the substrate 101 and patterned to expose a portion of the substrate 101 into which the opening 601 will be formed. The hard mask 103 may be a masking material such as silicon nitride, and may be formed using a process such as plasma enhanced chemical vapor deposition (PECVD). However, any other suitable hard mask material, such as silicon oxide, and any other process of formation, such as chemical vapor deposition (CVD), may alternatively be utilized. In an embodiment the hard mask 103 may be formed to a thickness of between about 500 Å and about 5000 Å, such as about 1900 Å.

Once formed, the hard mask 103 may be patterned to expose the substrate 101 using, e.g., a photolithographic masking and etching process. In such a process a photoresist (not illustrated in FIG. 1) may be placed on the hard mask 103. The photoresist may comprise a conventional photoresist material, such as a deep ultra-violet (DUV) photoresist, and may be deposited on the surface of the hard mask 103, for example, by using a spin-on process to place the photoresist. However, any other suitable material or method of forming or placing the photoresist may alternatively be utilized. Once the photoresist has been placed on the hard mask, the photoresist may be exposed to energy, e.g. light, through a patterned reticle in order to induce a reaction in those portions of the photoresist exposed to the energy. The photoresist may then be developed, and portions of the photoresist may be removed, exposing a surface of the hard mask, which may then be etched to remove the exposed portions, thereby patterning the hard mask.

FIG. 1 additionally illustrates a first cleaning process (represented in FIG. 1 by the arrows labeled 105) that may be performed prior to etching the substrate 101. This first cleaning process 105 may be performed in order to remove any residual materials from the surface of the substrate 101 and the hard mask 103 that may interfere with the subsequent etching process (not illustrated in FIG. 1 but illustrated and discussed below with respect to FIGS. 3-4). Such residues may include leftover polymer material from the photoresist used to pattern the hard mask 103 and metal particles that may have remained on the surface of the substrate 101.

In an embodiment the first cleaning process 105 maybe a Cessestte clean and may comprise dipping the substrate 101 and the hard mask 103 into a first cleaning solution. The first cleaning solution may be an aqueous solution of hydrochloric acid (HCl), hydrogen peroxide ($H_2O_2$), and water ($H_2O$) in a 1:1:10 ratio, and may be kept at a temperature of between about 50° C. and about 90° C. The substrate 101 and hard mask 103 may be immersed in the first cleaning solution for a duration of between about 5 min and about 30 min, such as about ten minutes.

Figure 2:
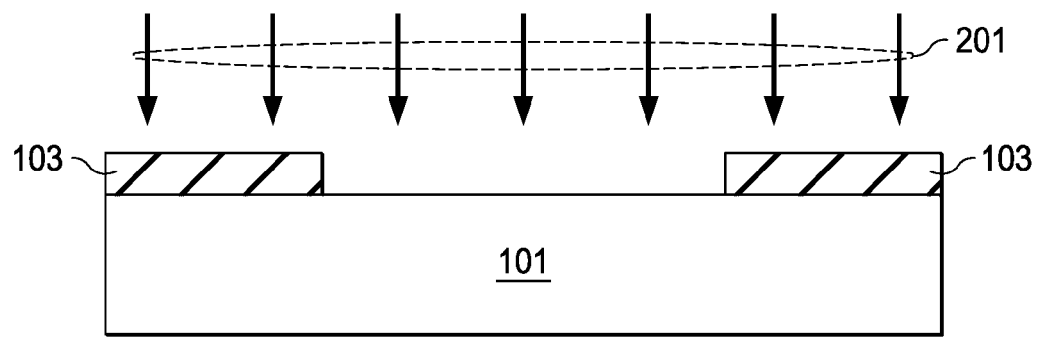
FIG. 2 illustrates a first rinse of the substrate and hard mask in accordance with an embodiment.

FIG. 2 illustrates that, after the first cleaning process 105 has been completed, the substrate 101 and hard mask 103 may be removed from the first cleaning solution and a first rinse and dry (represented in FIG. 2 by the arrows labeled 201) may be performed in order to remove any residual acid solution or base solution that may be present on the substrate 101 and the hard mask 103 after the first cleaning process 105. In an embodiment the first rinse 201 may be a rinse of, e.g., deionized water sprayed onto the substrate 101 and hard mask 103 at a temperature of between about 20° C. and about 30° C., such as about 25° C. However, any suitable rinsing medium, such as ultra-pure water or another suitable solvent, and any other rinsing technique, such as immersing the substrate 101 and the hard mask 103 into a tank of the rinsing medium, may alternatively be utilized to remove residues from the surface of the substrate 101 and the hard mask 103.

Figure 3:
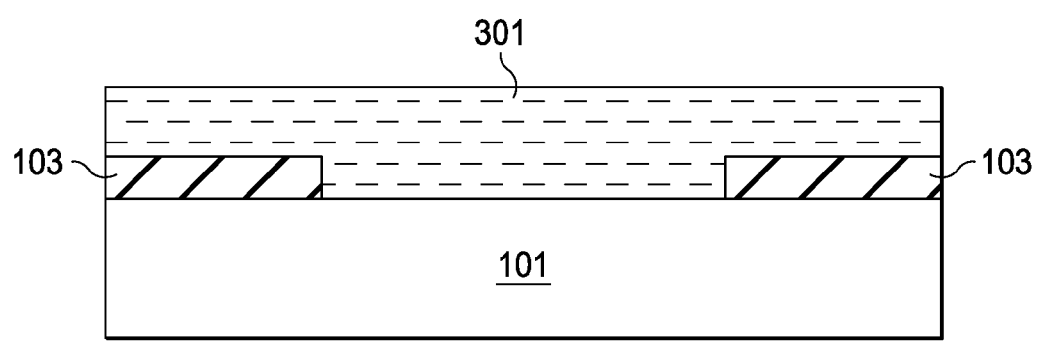
FIG. 3 illustrates placing the substrate into contact with an etching solution in accordance with an embodiment.

FIG. 3 illustrates that once the hard mask 103 has been patterned, the substrate 101 exposed by the hard mask 103 may be etched by placing the exposed portions of the substrate 101 into physical contact with an etching solution 301. In an embodiment the etching solution 301 may be placed in to contact with the substrate 101 using an wet etching process, whereby the etching solution 301 is placed into contact with the substrate 101 by immersing the substrate 101 into a tank or other container filled with the etching solution 301.

The etching solution 301 is utilized to remove those portions of the substrate 101 that are not protected by the hard mask 103 using a series of chemical reactions to react with and remove those portions of the substrate 101 into which the etching solution 301 is in βphysical contact. In an embodiment the etching solution 301 may be an aqueous solution with a high pH (such as greater than about 14) with multiple components such as a strong base, a surfactant, and an oxidizer. Together, these components in this solution may be utilized to etch the substrate 101 along the substrate's 101 crystallographic orientation. By etching along the crystallographic orientation of the substrate 101, the formation of the opening 601 may be controlled to provide a particular desired first angle α (not illustrated in FIG. 3 but illustrated and discussed further below with respect to FIG. 6), such as a 45° angle. Each of these components and their respective usages within the overall etching process are described further below in the following paragraphs.

Looking initially at the strong base, the strong base may be utilized to chemically react with the bulk of the material of the substrate 101 (e.g., silicon) and to anisotropically remove the material of the substrate 101 without removing the material of the hard mask 103. In an embodiment the strong base may be a base such as potassium hydroxide (KOH), although other suitable base reactants, such as sodium hydroxide (NaOH), may alternatively be utilized. The strong base may be in the aqueous solution at a concentration of between about 25%-wt and about 35%-wt, such as about 30%-wt.

However, strong bases such as KOH by themselves do not have the selectivity to control the etching process to etch along a desired crystallographic orientation of, e.g., the first angle α of about 45°. In particular, etching the substrate 101 with an aqueous solution of KOH would result in an angle of 54.7° or even 70° from a major surface of the substrate 101. As such, in order to modify the selectivity of the strong base to obtain the desired first angle α of about 45°, the surfactant may be added to the etching solution 301. In an embodiment the surfactant may be a ionic or non-ionic surfactant, and may be a surfactant with a sulfonated base, such as

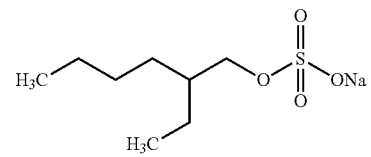

However, as one of ordinary skill in the art will recognize, surfactants with sulfonate bases are not the only surfactants that may be utilized. Rather, any suitable surfactant, such as surfactants with an alkyl base, such as alkyl polysaccharide, may be utilized. This and all such surfactants are fully intended to be included within the scope of the embodiments. In an embodiment the surfactant may have a concentration within the etching solution 301 of between about 0.01%-wt and about 0.4%-wt, such as about 0.15%-wt.

However, the inclusion of such surfactants within the etching solution 301 also creates additional issues during the process of etching the material of the substrate 101. In particular, during the etching reaction the surfactant will not only aid in the selectivity of the strong base but will also react with the strong base and the water in the etching solution 301 to form oil drops (not individually illustrated in FIG. 3) within the etching solution 301 and on the surface of the substrate 101. These oil drops may be up to a millimeter in size, and will be attracted to the material of the substrate 101 which is being etched. The attraction of the oil drops will interfere with the chemical reaction between the strong base, the surfactant, and the material of the substrate 101 by impeding the diffusion of the strong base and the surfactant, creating an unintended and undesired micromasking effect. This micromasking effect will interrupt the etching process in certain areas and cause the material of the substrate 101 to be unevenly etched.

In an embodiment, to counter this micromasking effect caused by undesired production of oil drops, an oxidant is added to the etching solution 301. The oxidant may be utilized to react with the material of the substrate 101 masked by the oil drop that has been attracted to the surface of the substrate 101. The oxidant will react with the material of the substrate 101 (e.g., silicon) and form an oxidized material such as silicon oxide beneath the oil drop. By oxidizing the material of the substrate 101, the material of the substrate 101 will be modified from being hydrophobic to being hydrophyllic, thereby suppressing or inhibiting hydrogen bonding between the material of the substrate 101 and the oil drop and, in effect, causing the material of the substrate 101 to repel the oil drop away from the surface of the substrate 101. Once the oil drop is away from the surface of the substrate 101, the micromasking effect has been removed and the strong base and surfactant may again work to etch the material of the substrate 101 and the oxidized material formed from the substrate 101.

In an embodiment the oxidant may be hydrogen peroxide ($H_2O_2$), although any suitable oxidant, such as ozone ($O_3$) or potassium permanganate ($KMnO_4$), may alternatively be utilized. Additionally, the oxidant may be present in the etching solution 301 in a concentration large enough to be able to react with the surface of the substrate 101 underneath an oil drop, but not so large as to dominate the overall reaction characteristics of the etching solution 301. In an embodiment, the oxidant may have a concentration in the etching solution 301 of between about 0.1%-wt and about 0.2%-wt.

During the etching process, the etching solution 301 may be kept at a temperature of between about 60° C. and about 80° C., such as about 70° C. The substrate 101 may be immersed in the etching solution 301 for a time of between about 40 min and about 120 min, such as about 70 min and at a depth of between about 40 μm and about 60 μm, such as about 50 μm. At such conditions the etching solution 301 will provide a well controlled etch rate of between about 0.4 μm/min and about 1.5 μm/min and will also help to prevent the reverse reaction of the etching process whereby hillocks and bubble hillocks may be regrown on the material of the substrate 101.

Figure 4:
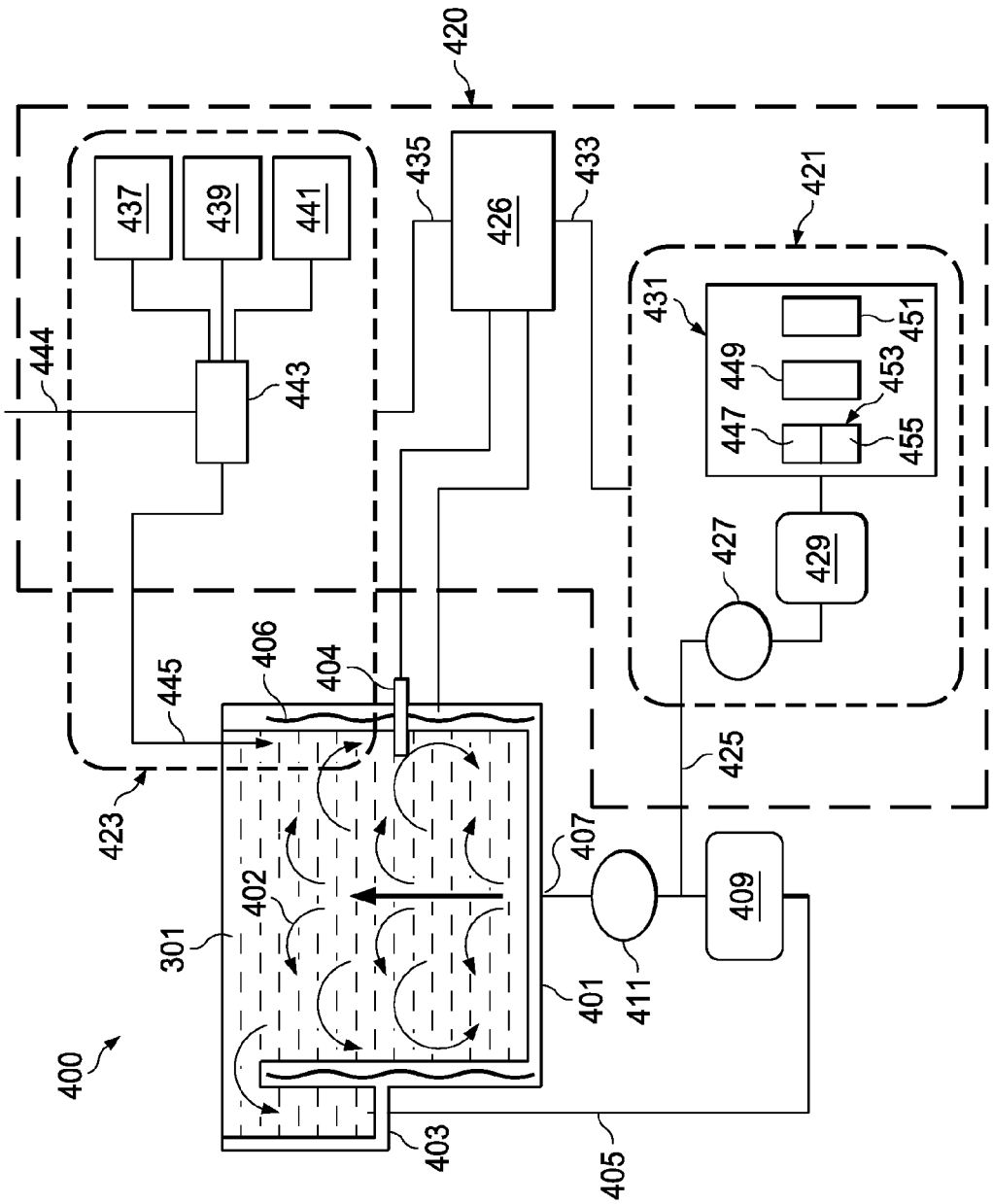
FIG. 4 illustrates a wet etching system that may be used to etch the substrate in accordance with an embodiment.

FIG. 4 illustrates a wet etching system 400 that may be utilized to bring the substrate 101 into contact with the etching solution 301. In an embodiment the wet etching system 400 may include a primary etching tank 401 with an overflow reservoir 403 and a recirculation line 405. In an embodiment the primary etching tank 401 holds the etching solution 301 and will receive the substrate 101 and hard mask 103 into the etching solution 301. As such, the primary etching tank 401 will be sized based at least in part upon the size of the substrate 101 that will be etched, and may be, e.g., a circular tank with a diameter of between about 13 inches and about 16 inches, such as about 14 inches.

In order to maintain circulation (represented in FIG. 4 by the curved arrows labeled 402) within the primary etching tank 401, which circulation helps to mix the etching solution 301 and aid in the replenishment of the etching solution 301 adjacent to the surface of the substrate 101, the primary etching tank 401 may additionally have an overflow reservoir 403. In an embodiment the overflow reservoir 403 is positioned to receive the etching solution 301 after the etching solution 301 has entered the primary etching tank 401 (e.g., through an entry port 407 at the bottom of the primary etching tank 401) and has circulated through the primary etching tank 401 before entering the overflow reservoir 403. As such, the overflow reservoir 403 may be a weir located adjacent to a top of the primary etching tank 401 so that etching solution 301 can enter the bottom of the primary etching tank 401, circulate around the primary etching tank 401, and make its way up through the primary etching tank 401 before overflowing a side of the primary etching tank 401 and entering the overflow reservoir 403.

In an embodiment the overflow reservoir 403 is connected to the recirculation line 405. The recirculation line 405 receives the etching solution 301 from the overflow reservoir 403 and recirculates the etching solution 301 from the overflow reservoir 403 back to the primary etching tank 401. In an embodiment the recirculation line 405 has a first pump 409 that is utilized to pump the etching solution 301 back into the primary etching tank 401 through, e.g., the entry port 407. The first pump 409 also helps to provide the forces that aid in the mixing of the etching solution 301 within the primary etching tank 401.

The recirculation line 405 may also comprise a filter 411. The filter 411 is used to remove particulate materials and other impurities from the etching solution 301 as the etching solution 301 recirculates within the wet etching system 400. These impurities may include silicate, aggregation surfactant, the oil drop by-products of the etching solution 301 (described above with respect to FIG. 3), and other particles that may form during the etching reactions or else otherwise be in the etching solution 301. The filter 411 may be sized, for example, to capture the impurities such as the silicate, the aggregation surfactant, and the oil drop by-products and, as such, may be dependent at least in part upon the size of these impurities. However, in an embodiment the filter 411 may remove particles having a size of between about 0.05 um and about 2 um, such as about 0.2 um.

The recirculation line 405, first pump 409, and filter 411 may be used to provide a desired recirculation rate of the etching solution 301 to the primary etching tank 401. This recirculation rate may be used to ensure that the etching solution 301 is properly mixed so that variations of concentrations (that result from the chemical reactions) at different points within the etching solution 301 are kept at a minimum. In an embodiment the recirculation rate may be controlled by the controller 426 and may be between about 5 L/min and about 20 L/min, such as about 10 L/min.

However, as the wet etching process continues, the reactants within the etching solution 301 (e.g., the strong base, the surfactant, and the oxidant) will react and their concentrations will reduce while concentrations of by-products of the reactions (such as silicate) will increase, thereby changing the various rates of reaction and introducing undesired complexities in attempts to control the etching process. In order to reduce the effects of this reduction, a replenishment system 420 is utilized to monitor the concentrations of the individual components and, if necessary, to replenish the individual components within the etching solution 301 in order to maintain better control over the etching process. In an embodiment the replenishment system 420 may comprise a monitoring system 421, a titration system 423, and a controller 426.

In an embodiment the monitoring system 421 may be tied in to the recirculation line 405 with a bypass line 425 connected between the first pump 409 and the filter 411. To obtain samples of the etching solution 301, a first valve 427 may be installed in the bypass line 425 and utilized to remove samples of the etching solution 301 from the recirculation line 405 for analysis. In an embodiment the first valve 427 may receive a signal from the controller 426 (discussed further below) to open and take a sample at regular intervals, such as about 2%-3% of the overall etching time. For example, with an etching time of about 2 hours, samples may be taken every 3 minutes.

In an embodiment, samples of the etching solution 301 taken from the recirculation line 405, after passing through the first valve 427, may need to be cooled down from the reaction temperature of the etching process (such as between about 60° C. and about 80° C.) prior to being analyzed. As such, a cooler 429 may be included in the bypass line 425 after the first valve 427 in order to provide the desired cooling of the samples of the etching solution 301. In an embodiment the cooler 429 may reduce the temperature of the sample of etching solution 301 to between about 20° C. and about 35° C., such as about 25° C.

To obtain the desired cooling the cooler 429 may be, e.g., a continuous flow heat exchanger with a cooling medium such as cooling water in order to get the samples of the etching solution 301 to a constant temperature. Alternatively, the cooler 429 may be an active cooling unit, e.g., a refrigeration unit to provide the desired cooling to the samples of the etching solution 301. Any suitable system and method of reducing the temperature of the sample of the etching solution 301 and maintaining the temperature of the samples of the etching solution 301 may be utilized, and all such systems and methods are fully intended to be included within the scope of the embodiments.

Once the samples of the etching solution 301 have been cooled to the appropriate temperature, the samples of the etching solution 301 can be analyzed by a measurement unit 431. In an embodiment the measurement unit 431 may be comprise one or more analysis units, with each of the analysis units utilized to measure one or more components of the etching solution 301. For example, a first analysis unit 447 may analyze the concentration of the oxidant, a second analysis unit 449 may analyze a concentration of the surfactant, and a third analysis unit 451 may analyze a concentration of the strong base.

In an embodiment the first analysis unit 447 used to measure the oxidant within the samples of the etching solution 301 may additionally comprise multiple measuring units, with each one of the individual different measuring units measuring different ranges of concentrations that the oxidant may be at. For example, for measuring relatively higher concentrations of the oxidant (e.g., above about 1000 ppm), the first analysis unit 447 may comprise an intensity unit 453 that measures, e.g., an oxidation-reduction potential (ORP) of the samples of the etching solution 301. Alternatively, the intensity unit 453 may be a pH measurement unit, which measures the pH of the samples of the etching solution 301. Either type of intensity unit 453 (e.g., that measures either ORP or pH) and any other suitable type of measuring unit that provides a suitable concentration of the oxidant within the etching solution 301 may be utilized, and all such types are fully intended to be included within the scope of the embodiments.

Additionally, for measurements that may be desired below the sensitivity levels of the intensity unit 453 (e.g., below 100 ppm), the first analysis unit 447 may also include a spectrum analysis unit 455. In an embodiment the spectrum analysis unit 455 may be an optical spectrum analysis unit, in which the sample of the etching solution 301 is irradiated with ultraviolet (UV) light, near-infra red (NIR) light, or infra-red (IF) light, and a resulting absorption spectrum is analyzed to determine the concentration of the oxidant within the samples of the etching solution 301.

Optionally, the spectrum analysis unit 455 may be utilized to measure the concentration of other components that may be within the etching solution 301. For example, the spectrum analysis unit 455 may be used to measure the concentration of reaction by-products, such as silicate, that may be within the etching solution 301. This and any other analysis for which the spectrum analysis unit 455 is suitable may also be utilized to provide information on the etching solution 301.

However, as one of ordinary skill in the art will recognize, while the first analysis unit 447 is described above as comprising an intensity unit 453 that measures an ORP and a spectrum analysis unit 455 that measures an absorption spectrum, these embodiments are intended to be illustrative and are not intended to be limiting. Rather, any suitable units that measure either a concentration of the oxidant or an indication of a concentration of the oxidant may alternatively be utilized, and all such measuring units are fully intended to be included within the scope of the embodiments.

Additionally, while the first analysis unit 447 is described herein as comprising a combination of an intensity unit 453 and a spectrum analysis unit 455, the embodiments are not so limited. Rather, the first analysis unit 447 may comprise only one of the intensity unit 453 or the spectrum analysis unit 455, or may comprise the intensity unit 453 or the spectrum analysis unit 455 in combination with other types of analysis units (not individually illustrated) in order to obtain a desired measurement of the concentration of the oxidant within the samples of the etching solution 301. Any suitable combination of systems may alternatively be utilized, and all such systems are fully intended to be included within the scope of the embodiments.

The second analysis unit 449 may be used to measure the concentration of the surfactant within the samples of the etching solution 301. In an embodiment the second analysis unit 449 may be a spectrum analysis unit, and may be an optical spectrum analysis unit, in which the samples of the etching solution 301 are irradiated with, e.g., ultraviolet (UV) light and a resulting absorption spectrum is analyzed to determine the concentration of the surfactant within the samples of the etching solution 301. In an embodiment the second analysis unit 449 may be the spectrum analysis unit 455 as described above with respect to the first analysis unit 447, although the second analysis unit 449 may have a separate spectrum analysis unit. Additionally, any suitable analysis unit may alternatively be utilized to measure the concentration of the surfactant within the samples of the etching solution 301.

The third analysis unit 451 may be used to measure the concentration of the strong base within the samples of the etching solution 301. In an embodiment in which the strong base is KOH, the third analysis unit 451 may be an pH meter to determine the concentration of KOH in the etching solution 301. However, any other suitable measurement system, such as a refractometer, may alternatively be utilized to measure the concentration of the strong base within the etching solution 301.

Additionally, the measurement unit 431 may also comprise measurement units to measure the concentration of the solvent (e.g., water) within the samples of the etching solution 301. In an embodiment the concentration of the solvent may be performed using the intensity unit 453 (described above), although a separate measurement unit used to solely measure the concentration of the solvent may alternatively be utilized.

Figure 5:
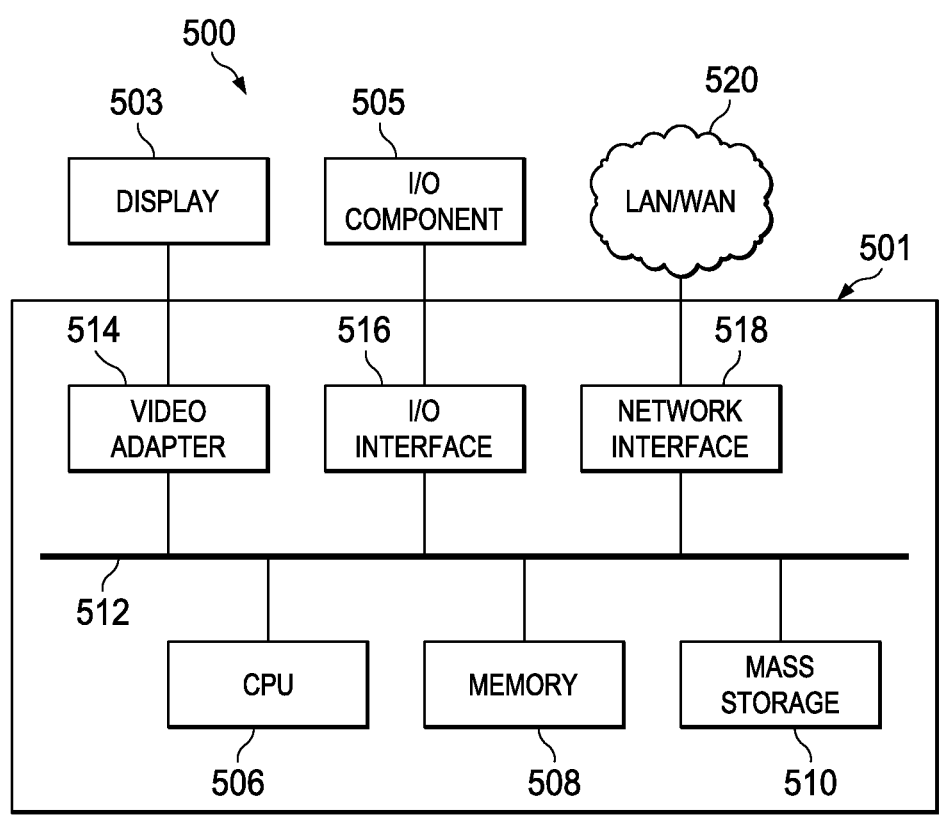
FIG. 5 illustrates a microcontroller that may be used in the wet etching system in accordance with an embodiment.

As the samples of the etching solution 301 are being analyzed, or after analysis of the samples of the etching solution 301 has been completed, the measurements taken by the monitoring system 421 are transmitted to the controller 426 through connection 433. FIG. 5 illustrates a system 500 that may be utilized for the controller 426. The controller 426 may be any form of computer processor that can be used in an industrial setting for controlling process machines or may alternatively be a general purpose computer platform programmed for such control. In an embodiment the controller 426 may comprise a processing unit 501, such as a desktop computer, a workstation, a laptop computer, or a dedicated unit customized for a particular application. The controller 426 may be equipped with a display 503 and one or more input/output components 505, such as instruction outputs, sensor inputs, a mouse, a keyboard, printer, combinations of these, or the like. The processing unit 501 may include a central processing unit (CPU) 506, memory 508, a mass storage device 510, a video adapter 514, and an I/O interface 516 connected to a bus 512.

The bus 512 may be one or more of any type of several bus architectures including a memory bus or memory controller, a peripheral bus, or video bus. The CPU 506 may comprise any type of electronic data processor, and the memory 508 may comprise any type of system memory, such as static random access memory (SRAM), dynamic random access memory (DRAM), or read-only memory (ROM). The mass storage device 510 may comprise any type of storage device configured to store data, programs, and other information and to make the data, programs, and other information accessible via the bus 512. The mass storage device 510 may comprise, for example, one or more of a hard disk drive, a magnetic disk drive, or an optical disk drive.

The video adapter 514 and the I/O interface 516 provide interfaces to couple external input and output devices to the processing unit 501. As illustrated in FIG. 5, examples of input and output devices include the display 503 coupled to the video adapter 514 and the I/O component 505, such as a mouse, keyboard, printer, and the like, coupled to the I/O interface 516. Other devices may be coupled to the processing unit 501, and additional or fewer interface cards may be utilized. For example, a serial interface card (not shown) may be used to provide a serial interface for a printer. The processing unit 501 also may include a network interface 518 that may be a wired link to a local area network (LAN) or a wide area network (WAN) 520 and/or a wireless link.

It should be noted that the controller 426 may include other components. For example, the controller 426 may include power supplies, cables, a motherboard, removable storage media, cases, and the like. These other components, although not shown in FIG. 5, are considered part of the controller 426.

Returning now to FIG. 4, the measurements of the measurement unit 431 are sent to the controller 426. The controller 426 uses the measurements to determine if one or more of the components of the etching solution 301 (e.g., the strong base, the surfactant, the oxidant, the water, etc.) need to be replenished in order to maintain a desired concentration of each component within the primary etching tank 401. If one or more components need to be replenished, for example if the concentration of the oxidant within the etching solution 301 dips below a threshold concentration for that component (e.g., below about 01%-wt), the controller 426 will determine that a makeup amount of the component (e.g., the oxidant) should be added to the etching solution 301 within the primary etching tank 401.

After the controller 426 determines that a makeup amount of one or more of the components needs to be added, the controller 426 will then determine how much of each components needs to be added. For example, using the measurements from the monitoring system 421 and other information such as the amount of the etching solution 301 within the system, the controller 426 can calculate how much of each component to add into the etching solution 301 in order to reach a desired concentration for each component. Alternatively, a lookup table with previously calculated amounts may be stored within the memory 508 of the controller 426 and referenced by the controller 426 to determine how much of each component may be added to reach the desired concentration for each component.

Once an amount of each component is determined, the controller 426 sends a signal through connection 435 to the replenishment system 420. The replenishment system 420 may be, e.g., a titration system and may comprise a first component storage unit 437 for storing a makeup amount of the strong base, a second component storage unit 439 for storing a makeup amount of the surfactant, and a third component storage unit 441 for storing a makeup amount of the oxidant. Each one of the first component storage unit 437, the second component storage unit 439, and the third component storage unit 441 may comprise a container suitable for holding, storing, and accessing the component within. For example, in the embodiment in which the strong base is KOH, the first component storage unit 437 may comprise a container resistant to KOH in order to prevent or reduce chemical degradation of the KOH prior to its use. Similarly, the second component storage unit 439 may comprise a material to store and protect the surfactant and the third component storage unit 441 may comprise a material to store and protect the oxidant. Any suitable material or shape may alternatively be utilized for the first component storage unit 437, the second component storage unit 439, and the third component storage unit 441.

In operation the controller 426, in response to the measurements received from the monitoring system 421, sends signals to the replenishment system 420 to supply a desired amount of each component to the primary etching tank 401. The replenishment system 420 receives the signals from the controller 426 and removes a desired amount of each component from the first component storage unit 437, the second component storage unit 439, and the third component storage unit 441. This removal may be performed by initiating one or more pumps (not individually illustrated in FIG. 4) attached to individual ones of the first component storage unit 437, the second component storage unit 439, and the third component storage unit 441 in order to remove a desired amount of the components from their respective containers and pump them, e.g., to a mixer 443.

However, pumps are not the only mechanism by which the individual components may be removed from their respective containers. In an alternative embodiment the components within the first component storage unit 437, the second component storage unit 439, and the third component storage unit 441 may be placed under pressure and valves may be placed along output ports (not individually illustrated in FIG. 4) of the first component storage unit 437, the second component storage unit 439, and the third component storage unit 441. The valves may then be individually activated for a time period by the signals from the controller 426, and the pressure will cause the components within the first component storage unit 437, the second component storage unit 439, and the third component storage unit 441 to flow to the mixer 443 without the need for a pump. Such a system, and any other system which may be used to store, extract, and send the individual components to the mixer 443 may alternatively be utilized, and all such systems are fully intended to be included within the scope of the embodiments.

Additionally, a makeup solvent line 444 may also be included within the replenishment system 420. In an embodiment in which the etching solution 301 is an aqueous solution comprising water as a solvent, the makeup solvent line 444 may provide an entry point for makeup water to be introduced to the system. The makeup solvent line 444 may be a pipe that receives solvent such as deionized water or ultrapure water from a source and routes the solvent to the mixer 443.

The mixer 443 receives the makeup amounts of one or more of the strong base, the surfactant, the oxidant, and/or the solvent and mixes the combination prior to their introduction into the primary etching tank 401. In an embodiment the mixer 443 may mix the components using the turbulence from their entry into the mixer 443. Alternatively, the mixer 443 may provide an active mixing action using, e.g., an agitator, to actively mix the components into a solution prior to sending them to the primary etching tank 401.

Once mixed, the makeup solution is removed from the mixer 443 and introduced into the primary etching tank 401 through, e.g., makeup line 445. In an embodiment the makeup line 445 introduces the makeup solution into the primary etching tank 401 such that the makeup solution will be sufficiently mixed with the etching solution 301 already within the primary etching tank 401 and the recirculation line 405 prior to the makeup solution coming into contact with, e.g., the substrate 101 during an etching process.

In an embodiment the combination of the monitoring system 421, the controller 426, and the replenishment system 420 may be used to control the various components within the etching solution 301 to withstand desired ranges. For example, the oxidant within the etching solution may be controlled to be within about +/−0.02%-wt of the desired concentration, the surfactant may be controlled to be within about +/−0.05%-wt of the desired concentration, and the strong base may be controlled to be within about +/−2%-wt of the desired concentration. By controlling these concentrations, along with controlling the temperature, recirculation rate, and the previous cleaning steps, the etching process may be controlled to achieve an etching rate of between about 0.4 μm/min and about 1.5 μm/min for between about 60 minutes and about 90 minutes.

By providing the makeup solution to the primary etching tank 401, the etching solution 301 within the primary etching tank 401 (and, hence, the etching solution 301 that is being used to etch the substrate 101) can be better controlled in real time. In particular, the concentration of the oxidant, the surfactant, and the strong base can be kept within the desired ranges so that the benefits of each component can be obtained while also reducing or eliminating the downside of using each component. As such, older, less efficient and more costly methods of monitoring the etching solutions, such as determining direct damage using SEM measurements that do not provide for immediate adjustments and control, may be avoided.

A heater 406 controlled by the controller 426 may additionally be placed around the primary etching tank 401 in order to control the temperature of the chemical reactions within the primary etching tank 401. The heater 406 may be, e.g., a resistive heater and may have temperature sensors 404 in order to provide heating information to the controller 425. The temperature sensors 404 may be, e.g., a thermocouple installed within the primary etching tank 401 or, alternatively, either within the recirculation line 405 or taken from the samples of the etching solution, in order to monitor the temperature of the etching solution 301. However, any suitable type of sensor may alternatively be utilized to measure the temperature of the heater 404 and transmit that measurement to the controller 426.

In an embodiment the controller 425 receives temperature readings from the temperature sensors 404 and determines the amount of heating that may be necessary in order to maintain the temperature of the etching solution 301. For example, the controller 425 may control the heater 406 to provide a constant temperature within +/−1° C. of the desired reaction temperature (e.g., a reaction temperature of between about 50° C. and about 90° C.). However, any suitable range of temperatures that provides the desired amount of control of the reaction rates may alternatively be utilized.

Figure 6:
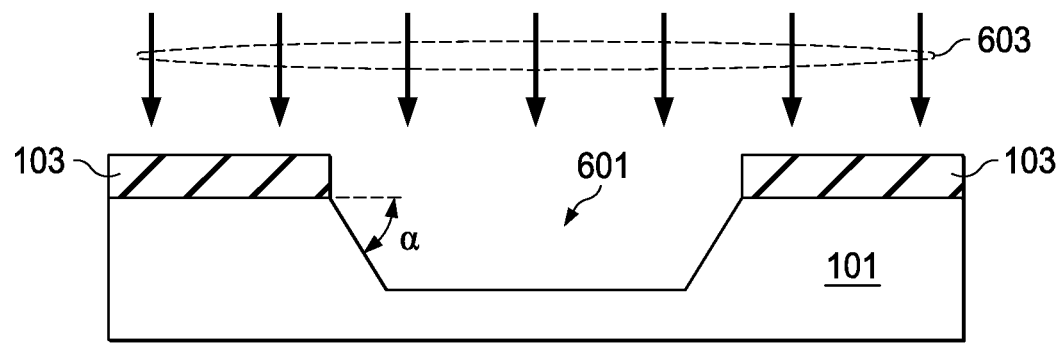
FIG. 6 illustrates a resulting structure of the etching process in accordance with an embodiment.

FIG. 6 illustrates a result of using the etching solution 301 described above to etch the substrate 101. As can be seen, the opening 601 is formed within the substrate 101 and the sidewalls of the opening 601 may be selectively etched to have a first angle α of about 45° with a major surface of the substrate 101. Additionally, with the inclusion of the oxidant within the etching solution 301 the sidewalls and bottom of the opening 601 are formed with a smoother surface due to the lack of micromasking from the oil drops that are formed between the surfactant, the strong base, and the water within the etching solution 301. Additionally, the inclusion of the oxidant will also work to inhibit or impede the reverse chemical reaction and help to prevent hillock regrowth during the etching process.

FIG. 6 also illustrates that, after the wet etching process has been completed, the substrate 101 and the hard mask 103 may be removed from the etching solution 301 and a second rinse and dry (represented in FIG. 6 by the arrows labeled 603) may be performed in order to remove any residual etching solution 301 that may be present on the substrate 101 and the hard mask 103 after the etching process. In an embodiment the second rinse 603 may be a rinse of, e.g., deionized water sprayed onto the substrate 101 and hard mask 103 at a temperature of between about 20° C. and about 35° C. such as about 25° C. However, any suitable rinsing medium, such as ultra-pure water or another suitable solvent, and any other rinsing technique, such as immersing the substrate 101 and the hard mask 103 into a tank of the rinsing medium, may alternatively be utilized to remove residual etching solution from the surface of the substrate 101 and the hard mask 103.

Figure 7:
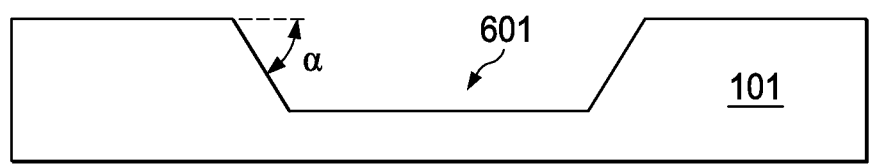
FIG. 7 illustrates a removal of the hard mask from the substrate in accordance with an embodiment.

FIG. 7 illustrates a removal of the hard mask 103 after the patterning of the substrate 101. In an embodiment the hard mask 103 may be removed with a wet etching process and an etchant such as an aqueous solution of hydrogen fluoride (HF) in a ratio between 1:5 and 1:100. The hard mask 103 may be removed by immersing the substrate 101 and the hard mask 103 into the etchant at a temperature of between about 50° C. and about 90° C., such as about 60° C. for a time period of between about 10 min and about 40 min, such as about 30 min.

Figure 8:
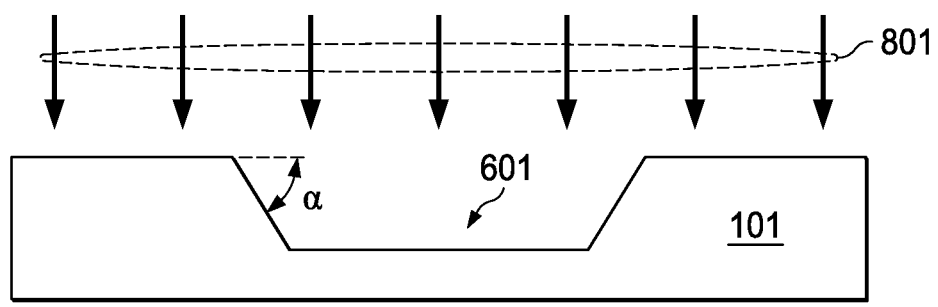
FIG. 8 illustrates a rinse of the substrate after the hard mask has been removed in accordance with an embodiment.

FIG. 8 illustrates that, after the hard mask 103 has been removed, the substrate 101 may be removed from the etchant and a third rinse and dry (represented in FIG. 8 by the arrows labeled 801) may be performed to remove any residual etchant left over by the removal of the hard mask 103. In an embodiment the third rinse 801 may be a rinse of, e.g., deionized water sprayed onto the substrate 101 at a temperature of between about 20° C. and about 35° C., such as about 25° C. However, any suitable rinsing medium, such as ultra-pure water or a suitable solvent, and any other rinsing technique, such as immersing the substrate 101 into a tank of the rinsing medium, may alternatively be utilized to remove residual etching solution from the surface of the substrate 101. After the third rinse 801, the substrate 101 may be dried using, e.g., by rinsing the substrate 101 with IPA and then placing the substrate 101 into a wafer dryer (not individually illustrated in FIG. 8).

Figure 9:
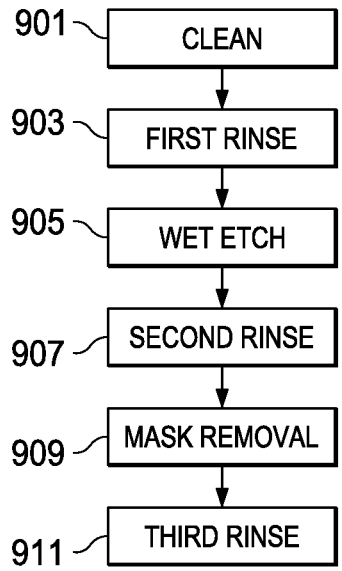
FIG. 9 illustrates a process flow that may be used to etch the substrate in accordance with an embodiment.

FIG. 9 illustrates a flow chart that may be utilized to pattern the substrate 101. In a first patterning step 901 the substrate 101 is cleaned with a first cleaning solution and then, in a second patterning step 903, the substrate 101 is rinsed. In a third patterning step 905, the substrate is patterned using a wet etch process and, in a fourth patterning step 907, the substrate 101 is rinsed again with a second rinse. In a fifth patterning step 909 the hard mask 103 is removed from the substrate 101 and, in a sixth patterning step 911, the substrate 101 is again rinsed with a third rinse.

Figure 10:
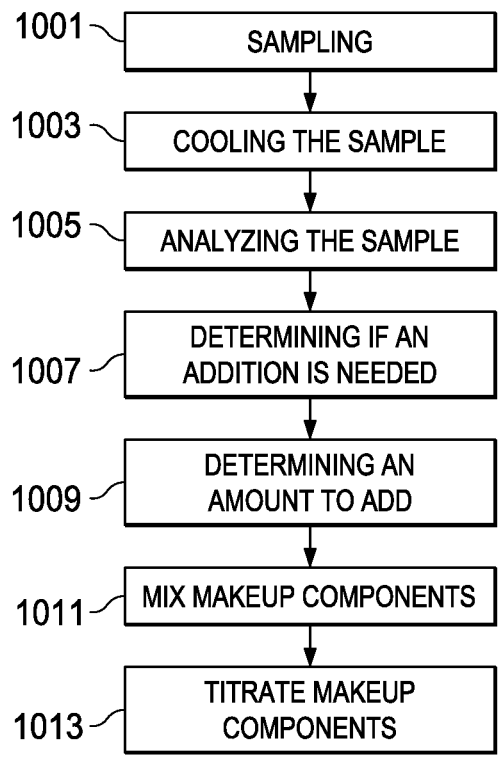
FIG. 10 illustrates a process flow that may be used to maintain the etching solution in accordance with an embodiment.

FIG. 10 illustrates a flow chart that may be utilized to maintain the concentrations of the components within the etching solution 301. In an embodiment a sample is removed from the etching solution in a first makeup step 1001 and the sample is cooled in a second makeup step 1003. The sample is then analyzed in a third makeup step 1005 to determine the concentrations of the components to be analyzed, and a determination is done as to whether an addition of makeup components is needed in a fourth makeup step 1007. If a determination is made that an addition is needed, an amount to be added is determined in a fifth makeup step 1009. Finally, the makeup components to be added are mixed together is a sixth makeup step 1011 and then added to the etching solution in a seventh step 1013.

Figure 11A:
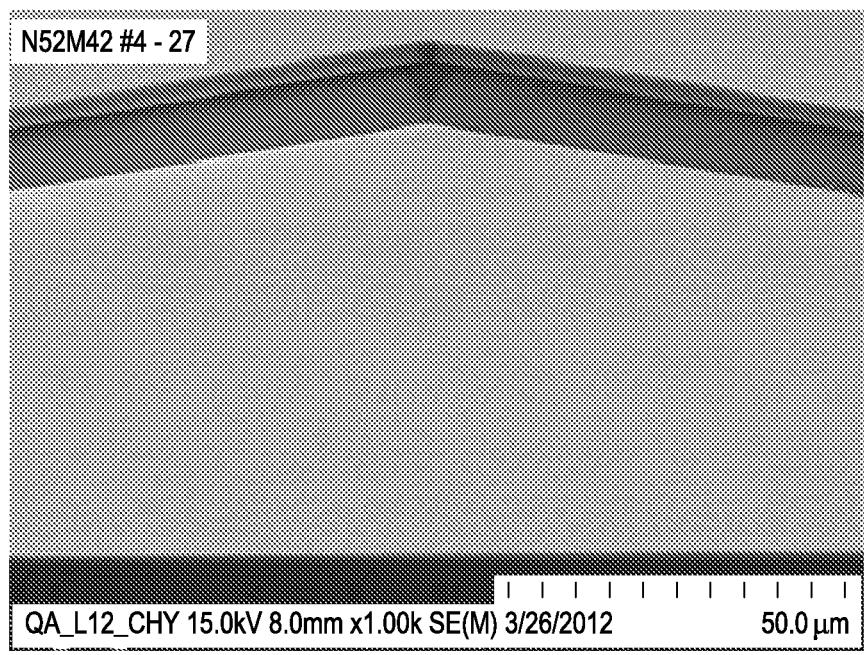
FIGS. 11A-11B illustrate test results between using a described etchant in accordance with an embodiment and using etchants not as described.
Figure 11B:
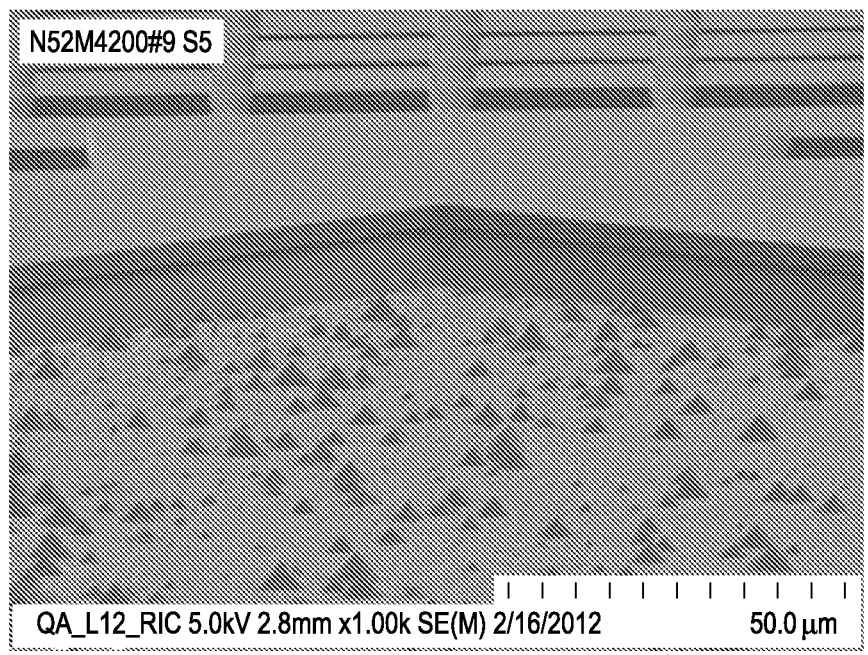

By maintaining a consistent control over the concentrations of the various components within the etching solution 301 during the etching process, the surface of the substrate 101 may be formed with a smooth surface and a reduced number of regrown hillocks. Such a smooth surface is additionally illustrated in FIGS. 11A-11B, with FIG. 11A illustrating the smooth surface of a material etched utilizing the etching solution 301 described above with respect to FIG. 3 and FIG. 11B illustrating an enlarged surface of a substrate etched with an etching solution of IPA and KOH. As can be seen, the material etched without the inclusion of the oxidant is uneven and rough, with hillocks forming throughout the surface. However, with the use of the etching solution 301 as described, the hillocks are removed along with the rest of the material, resulting in a much smoother and better controlled etching process.

By monitoring the individual components of the etching solution 301 such as the oxidant, the wet etching system 400 may be able to determine quickly when the levels of the individual components are outside of their desired ranges. By determining this quickly, makeup amounts of each component may be added to the etching solution 301 in order to restore the appropriate concentrations. By keeping the appropriate concentrations in the etching solution 301, better control may be achieved and a more efficient etching process may be obtained and the benefits of the etching solution 301 as described may be maintained through multiple etching processes.

In accordance with an embodiment, a system for etching a semiconductor device comprising a primary etch tank and a monitoring unit comprising an oxidant analysis unit is provided. A makeup unit comprises an oxidant storage unit.

In accordance with another embodiment, a system for etching a semiconductor device comprising an etching tank with an inlet port, and outlet port, and a makeup port is provided. A recirculation line is connected to the inlet port and the outlet port, the recirculation line comprising a filter to remove an oil by-product, wherein the etching tank and the recirculation line are an etching system. A by-pass line is connected between the etching system and a monitoring system, the monitoring system comprising an oxidant analysis unit, and a makeup unit is in communication with the monitoring system, the makeup unit comprising an oxidant makeup storage unit.

In accordance with yet another embodiment, a method of etching a semiconductor device comprising removing a sample from an etching solution and analyzing the sample to determine a concentration of an oxidant within the sample is provided. A makeup amount of the oxidant is introduced into the etching solution based upon the concentration of the oxidant from analyzing the sample.

Although the present embodiments and their advantages have been described in detail, it should be understood that various changes, substitutions and alterations can be made herein without departing from the spirit and scope of the disclosure as defined by the appended claims. For example, the precise components utilized for the etching solution may be adjusted to obtain the desired etching characteristics. Additionally, the different types of analysis units used to measure the concentrations of the different components may be modified while still remaining within the scope of the embodiments. Additionally, the etching processes discussed herein may be used in a wide variety of applications, such as optical products, microelectromechanical (MEMS) structures, and light emitting diode (LED) manufacturing such as forming V-grooves and waveguide trenches.

Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A system for etching a semiconductor device comprising:
    a primary etch tank configured to hold an etchant;
    a monitoring unit comprising an oxidant analysis unit; and
    a makeup unit comprising:
        an oxidant storage unit for storing an oxidant;
        a base storage unit for storing a base; and
        a surfactant storage unit for storing a surfactant;
    a mixing unit coupled to a first output from the oxidant storage unit, a second output from the base storage unit, and a third output from the surfactant storage unit.

2. The system of claim 1, wherein the oxidant analysis unit is an oxidation reduction potential measurement unit.

3. The system of claim 1, wherein the oxidant analysis unit is an optical spectrum analysis unit.

4. The system of claim 3, wherein the optical spectrum analysis unit is a UV absorption spectrum analysis unit.

5. The system of claim 1, wherein the oxidant analysis unit comprises:
    an oxidation reduction potential measurement unit; and
    an optical spectrum analysis unit.

6. The system of claim 1, wherein the oxidant is $H_2O_2$.

7. The system of claim 1, further comprising:
    a recirculation line; and a by-pass line connected to the recirculation line and to the monitoring unit.

8. A system for etching a semiconductor device comprising:
  an etching tank configured to hold an etchant with an inlet port, and outlet port, and a makeup port;
  a recirculation line connected to the inlet port and the outlet port, the recirculation line comprising a filter to remove an oil chemical-reaction by-product, wherein the etching tank and the recirculation line are an etching system;
  a by-pass line connected between the etching system and a monitoring system, the monitoring system comprising an oxidant analysis unit; and
  a makeup unit in communication with the monitoring system, the makeup unit comprising an oxidant makeup storage unit.

9. The system of claim 8, wherein the makeup unit is in communication with the monitor system through a microcontroller.

10. The system of claim 8, wherein the monitoring system further comprises a cooler.

11. The system of claim 8, wherein the makeup unit further comprises:
  a makeup base storage unit; and
  a makeup surfactant storage unit.

12. The system of claim 8, wherein the outlet port is an overflow reservoir.

13. The system of claim 8, wherein the oxidant analysis unit further comprises:
  an oxidation reduction potential measuring unit; and
  an optical spectrum analysis unit.

14. The system of claim 13, wherein the monitoring system further comprises a surfactant measurement unit.

15. A system for etching a semiconductor device, the system comprising:
  an etching tank configured to hold an etchant;
  a recirculating pump to pump etchant through a recirculation line;
  a monitoring unit comprising:
    a sample valve connected to the recirculation line;
    an oxidant analysis unit connected to the sample valve, wherein the oxidant analysis unit comprises an oxidation reduction potential measurement unit;
  a makeup unit comprising:
    an oxidant storage unit with a first outlet;
    a base storage unit with a second outlet;
    a surfactant storage unit with a third outlet;
    a mixing unit coupled to the first outlet, the second outlet and the third outlet, the mixing unit comprising a fourth outlet; and
    an makeup line connecting the fourth outlet to the etching tank.

16. The system of claim 15, further comprising a solvent makeup line connected to the mixing unit.

17. The system of claim 15, further comprising a controller connected to both the monitoring unit and the makeup unit.

18. The system of claim 15, further comprising a chilling unit connected to an output of the sample valve.

19. The system of claim 15, wherein the makeup unit is a titration unit.

20. The system of claim 15, wherein the etching tank further comprises a weir.

* * * * *